United States Patent [19]

Riccardi et al.

[11] 4,178,102
[45] Dec. 11, 1979

[54] PROCESS AND APPARATUS FOR MEASURING THE CONCENTRATION OF A MOLECULE OF SELECTIVE SPECTRUM IN A SAMPLE SUBSTANCE

[75] Inventors: Clemente C. Riccardi; Sergio Meda; Luciano Cigognini, all of Milan, Italy

[73] Assignee: U.S. Philips Corporation, New York, N.Y.

[21] Appl. No.: 834,956

[22] Filed: Sep. 20, 1977

[51] Int. Cl.$^2$ ............................ G01J 3/36; G01J 3/30
[52] U.S. Cl. .................................. 356/307; 250/458; 250/459; 356/318
[58] Field of Search ..................... 356/85, 82, 75, 301, 356/307, 317, 318; 250/458, 459

[56] References Cited

U.S. PATENT DOCUMENTS

| | | | |
|---|---|---|---|
| 3,520,614 | 7/1970 | Goldstein | 356/85 |
| 3,625,613 | 12/1971 | Abell et al. | 356/75 |
| 3,811,778 | 5/1974 | Hadeishi | 356/85 |
| 3,832,555 | 8/1974 | Ohnishi | 250/458 |
| 4,022,531 | 5/1977 | Orazio et al. | 356/100 |
| 4,035,083 | 7/1977 | Woodriff et al. | 356/82 |

*Primary Examiner*—Vincent P. McGraw
*Attorney, Agent, or Firm*—Thomas A. Briody; Edward J. Connors, Jr.; Paul R. Miller

[57] ABSTRACT

A method and apparatus are described for measuring the concentration of a molecule of selective spectrum in a sample substance in which errors from spurious light signals due to diffused light or from spurious fluorescent or phosphorescent light due to traces of other molecules in the sample substance are eliminated. The invention subjects the sample substance to light of a first wavelength in the absorption spectrum of the molecule to be measured and obtains a signal representative of light emission from the molecule with the spurious light signals superimposed thereon. Thereafter, the sample substance is subjected to a second excitation light having a wavelength close to the first wavelength but outside of the absorption and emission spectra of the molecule to be measured to generate a second signal representative of light emission from the molecule to be measured, which light emission results only from diffusion light and/or fluorescent or phosphorescent light due to traces of other molecules in the sample substance. A differentiator then generates a signal of the difference of the first and second signals, which is representative of the true light emission signal of the molecule to be measured.

8 Claims, 5 Drawing Figures

PROCESS AND APPARATUS FOR MEASURING THE CONCENTRATION OF A MOLECULE OF SELECTIVE SPECTRUM IN A SAMPLE SUBSTANCE

This invention relates to a process and apparatus for measuring the concentration of a molecule of selective spectrum in a sample substance.

Many organic molecules (for example phenolic molecules) notably present very selective absorption and fluorescent or phosphorescent emission spectra, i.e. with very accentuated upward and downward fronts.

A normal method for measuring the concentration of a molecule of this kind in a sample substance (mostly an aqueous solution of said molecule) notably consists of radiating the sample with monochromatic excitation light having a wavelength lying in the absorption spectrum of the molecule, then filtering and collecting the corresponding fluorescent or phosphorescent light emitted by the sample substance at a higher wavelength, and finally measuring the intensity of the collected light. The measured intensity is notably an indication of the concentration of the molecule under examination in the sample substance.

Although this measuring method has various merits which make it preferred to other possible methods, it suffers from the disadvantage of providing a measurement which does not take into account inaccuracies due to inevitable superimposing on the useful signal of spurious signals originating from diffused light and/or spurious fluorescent light emitted by traces of other molecules contained in the sample substance.

The object of the present invention is to provide a process and apparatus which enable phenolic molecule concentration measurements to be made free from inaccuracies due to spurious signals superimposed on the useful signal emitted by the molecule under examination when excited.

The invention provides a measuring process comprising subjecting the sample substance to a first monochromatic excitation light of wavelength lying within the absorption spectrum of the molecule under measurement, filtering and collecting a first light emission from the sample substance at a wavelength lying within the emission spectrum of the molecule, and determining the intensity of the monochromatic light collected, and further comprising subsequently subjecting the sample substance to a second monochromatic excitation light of wavelength close to that of the first monochromatic light but outside the absorption and emission spectra of the molecule, filtering and collecting a corresponding second light emission from the sample substance at the same wavelength as the first, then determining the new intensity of collected light and subtracting this from the first to give a useful monochromatic signal free from spurious signals due to diffused light or to spurious fluorescent or phosphorescent light due to traces of other molecules in the sample substance.

The measuring apparatus according to the invention comprises an excitation monochromator arranged to subject the sample substance to a first monochromatic excitation light and subsequently to a second monochromatic excitation light of wavelengths which are close together but which are within the absorption spectrum of the molecule being measured and outside the absorption and emission spectra of the same molecule, respectively, a collection monochromator arranged to filter and collect corresponding light emissions from the sample substance at a wavelength within the molecule emission spectrum, and electronic processing means arranged to determine the collected light intensities corresponding to said emissions and substract one from the other.

In substance, the present invention therefore consists of a process and apparatus based on the use not of one but of two monochromatic excitation lights of close wavelengths, one of which, falling within the absorption spectrum of the molecule under examination, causes emission of a fluorescent or phosphorescent monochromatic light constituting the useful signal and on which are inevitably superimposed spurious signals due to diffused light and to possible fluorescent or phosphorescent light emitted by traces of different molecules, while the other, being of a wavelength outside the absorption and emission spectra of the molecule under examination, only causes emission of a spurious light signal due to the diffused light and, if they exist, possible fluorescent or phosphorescent light emitted by traces of other molecules. As the spurious signals are equal (or substantially equal) for the two excitation wavelengths, it is evident that the final subtraction of the two collected light signals leads to mutual cancellation of the spurious signals and consequent isolation of just the useful signal representing the effective concentration of the molecule under examination in the sample substance. The double monochromatic excitation provided by the present invention thus enables the inaccuracy factors accompanying the known single monochromatic excitation method to be eliminated.

It has already been stated that the second monochromatic excitation light has a wavelength close to the first but outside the absorption and emission spectra of the molecule under examination. In reality, the wavelength of said second monochromatic light should preferably lie within the space between the two spectra if both the spurious signals due to diffused light and those due to the interfering light emitted by traces of other molecules contained in the sample substance are to be eliminated, and it should be just greater than the maximum wavelength of the emission spectra of the molecule under examination if it is required to eliminate only the spurious signals due to diffused light or if it is not technically possible to operate the second monochromatic light excitation at a wavelength between two spectra. As these latter are usually spaced apart by approximately 30 nm the distance between the two excitation wavelengths may therefore vary from about 15 to about 60 nm. Mostly, it will not be a case of individual wavelengths but of very narrow wavebands, which could vary from 0.1 to 10 nm according to the type of molecule under examination and various other constructional and operational factors. Likewise the isolated and collected wavelength for the fluorescent or phosphorescent light emitted by the sample substance will not have a single value, but will in reality consist of a narrow waveband variable from 1 to 100 nm according to the actual circumstances.

Preferably the two monochromatic excitation lights are emitted in very rapid time succession, so as to allow the measurement to be possibly made on flowing samples, i.e. samples in movement relative to the measuring apparatus. In particular the time lag preferably varies from 0.1 to 10 μsec.

This obviously creates some problems with regard to the choice of the most suitable monochromator, because the most normal commercially available monochromators which have various moving parts are unable to be used for very rapid change-over from one wavelength to another. According to the invention, this problem is preferably solved by using an entirely static monochromator (based only on very rapid alternating illumination of two lamps) as described in U.S. Pat. No. 4,022,531, to which reference should be made for further details.

These and further characteristics of the present invention will be evident from the detailed description given hereinafter of one possible embodiment illustrated by way of example in the accompanying drawings, in which.

Figure 1:
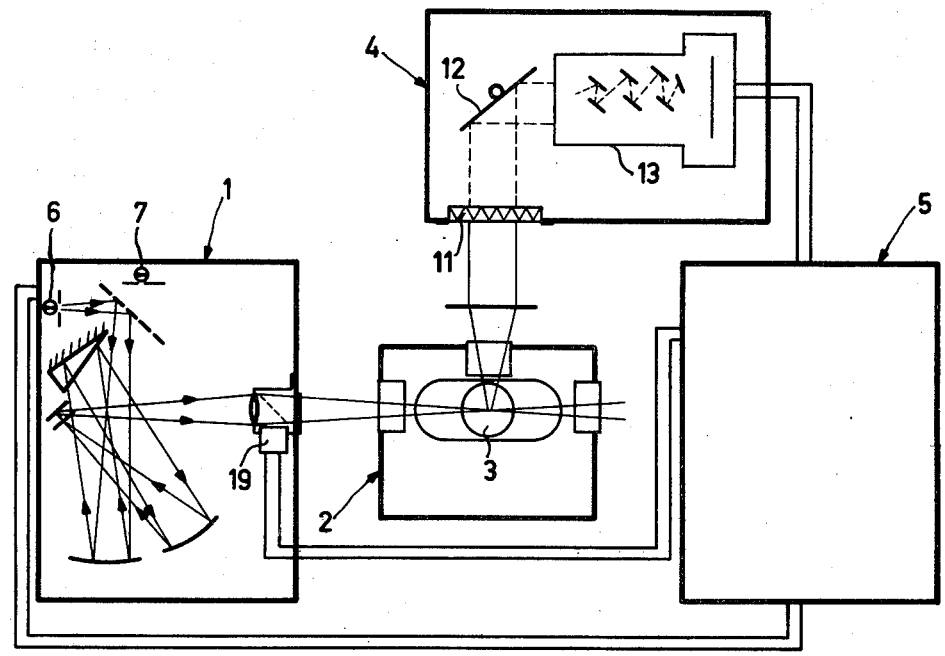
FIG. 1 is a diagrammatic overall view of a measuring apparatus according to the present invention.
Figure 2:
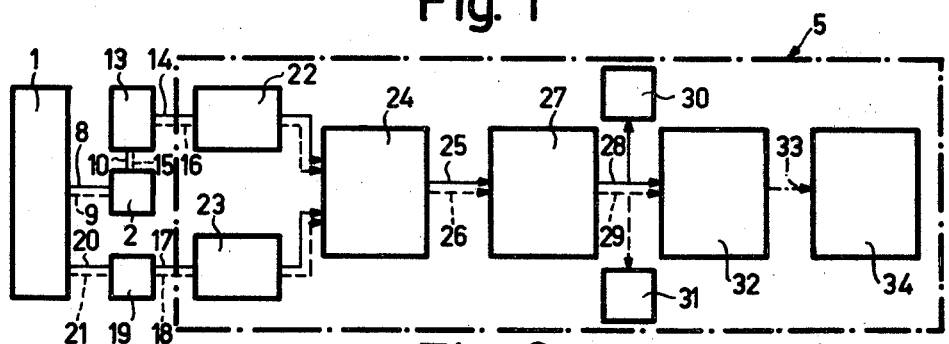
FIG. 2 shows the same apparatus in greater detail.

The measuring apparatus shown on the drawings, and in particular in FIGS. 1 and 2, generally comprises an excitation monochromator 1, a sample cell 2 containing the sample substance 3 for which the concentration of a determined molecule of selective spectrum is to be measured (for example a phenol in aquous solution), a measuring monochromator 4 and finally an analogue, digital or mixed electronic processor 5.

The excitation monochrometer 1 is of the static type described in U.S. Pat. No. 4,022,531, and comprises two lamps 6 and 7 which are alternately illuminated in rapid succession (repeated several times) to produce corresponding monochromatic excitation lights 8 and 9 (FIG. 2) very close together in time (0.1 to 10 $\mu$sec) and of wavelengths $\lambda_1$ and $\lambda_2$ which are also very close (15 to 60 nm apart).

Figure 3:
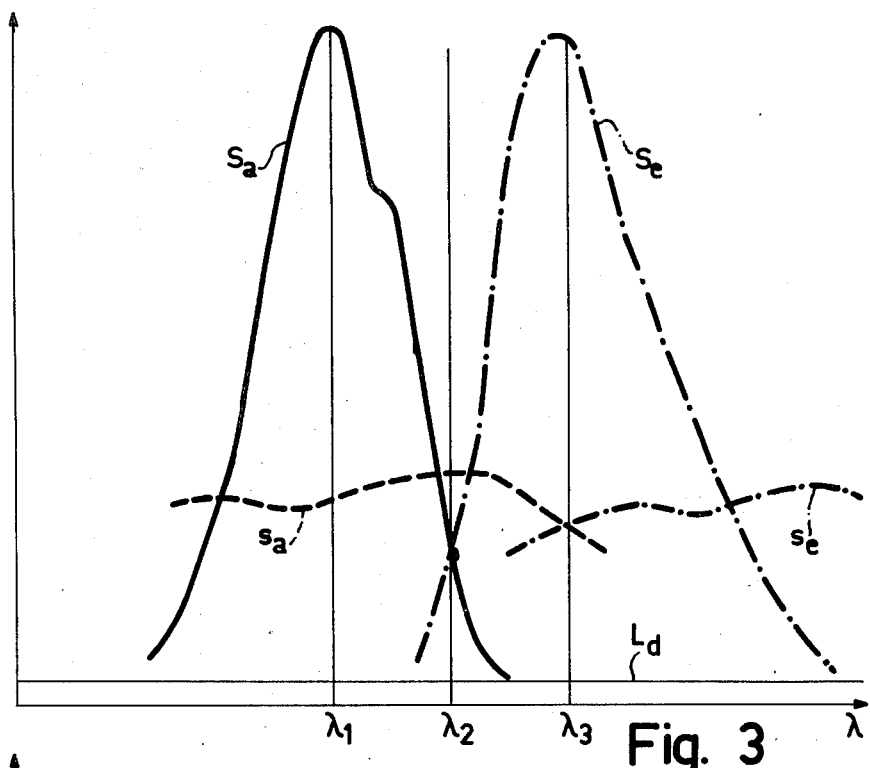
FIGS. 3 and 4 show the location of the excitation wavelength and fluorescent or phosphorescent emission wavelength relative to the absorption and emission spectra of the molecule under examination when eliminating all of the spurious signals, and when eliminating only the spurious signals due to diffused light respectively.
Figure 4:
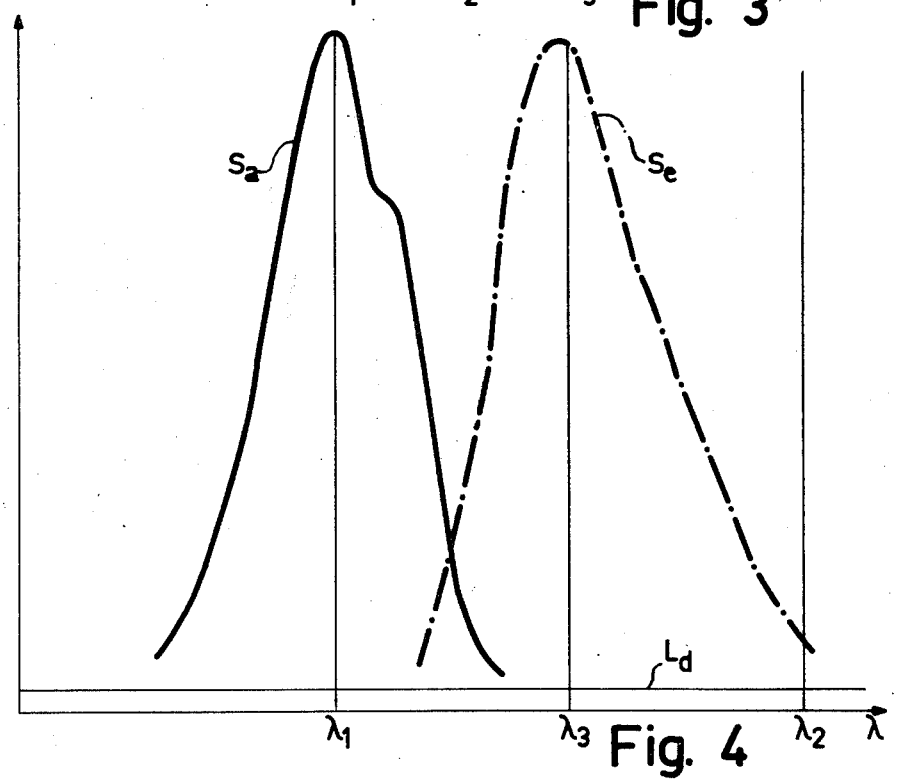

It will be assumed that the molecule under examination has an absorption spectrum $S_a$ and emission spectrum $S_e$ shown in FIGS. 3 and 4, accompanied by a constant diffused light $L_d$ and possible secondary spectra $s_a$ and $s_e$ (FIG. 3) due to traces of other molecules in the same substance.

If the wavelength $\lambda_1$ of a first monochromatic excitation light is made substantially to coincide with the center of the absorption spectrum $S_a$, as is in fact done, the molecule thus excited emits a corresponding fluorescent (or phosphorescent) light at a corresponding wavelength $\lambda_3$ substantially coinciding with the center of the emission spectrum $S_e$. The main emission of light has superimposed on it at wavelength $\lambda_3$ a certain diffused light $L_d$ and, in certain cases, an emission of secondary light due to the excitation effect determined by the light of $\lambda_1$ falling on possible traces of molecules of spectra $s_a$ and $s_e$ also present in the sample substance.

The light signal of wavelength $\lambda_3$ thus emitted, indicated in FIG. 2 by the reference numeral 10, and consisting in practice of a useful signal of monochromatic light emitted by the molecule under examination and, superimposed thereon, a spurious signal due to the interference of diffused light and, possibly, monochromatic light emitted by traces of other molecules, is filtered and collected by the measuring monochromator 4, which for this purpose comprises an inlet filter 11 of very narrow band centered at $\lambda_3$, a positionable mirror 12 and a photomultiplier 13 for converting the weak light signal 10 into an amplified electrical signal 14 (FIG. 2).

While the wavelength $\lambda_1$ of the first monochromatic excitation light is substantially centered on the absorption spectrum $S_a$ of the molecule under examination, the wavelength $\lambda_2$ of the second monochromatic excitation light is located outside said absorption spectrum, namely between the two spectra $S_a$ and $S_e$ (FIG. 3) or at a value greater than $S_e$ (FIG. 4). It is therefore not able to excite the molecule under examination to make it emit, as in the case of $\lambda_1$, a fluorescent or phosphorescent light of wavelength $\lambda_3$, but is however able to provide the measuring monochromator 4 with a spurious light signal 15 of wavelength $\lambda_3$ (FIG. 2) which coincides exactly with the spurious part of the signal 10 determined by the previous excitation at $\lambda_2$, and represents in the case of FIG. 3 both the diffused light and the monochromatic light emitted by the traces of molecules with spectra $s_a$ and $s_e$, and in the case of FIG. 4 only the diffused light $L_d$.

The spurious light signal 15 is filtered by the filter 11 and converted into a corresponding electrical signal 16 by the photomultiplier 13, from which two signals are emitted repeated several times in rapid succession, namely a signal 14 due to the excitation at wavelength $\lambda_1$ and comprising the useful signal with a spurious signal superimposed thereon, and a signal 16 due to the excitation at wavelength $\lambda_2$ and comprising only a spurious signal of value equal to that of the spurious signal contained in the signal 14.

Figure 5:
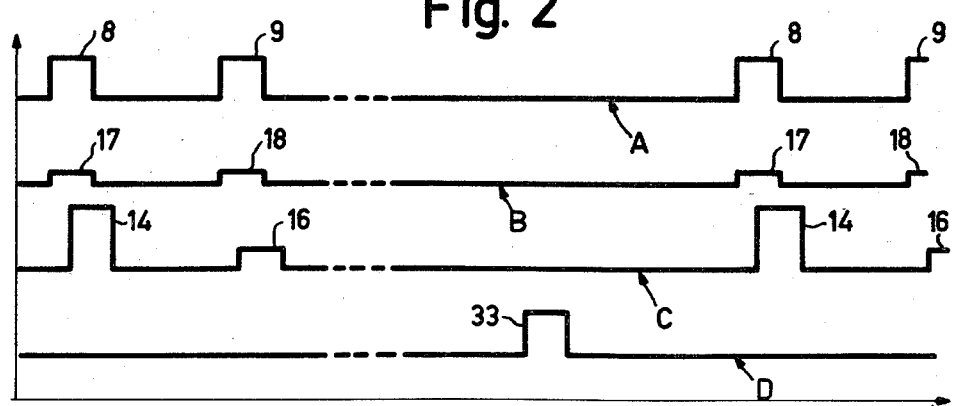
FIG. 5 shows various superimposed wave forms representing the method of operation of the apparatus.

The signals 14 and 16, of obviously different amplitude, are shown graphically by the wave form C of FIG. 5, the wave form A representing the pattern of the monochromatic excitation light signals 8 and 9, clearly of equal amplitude, and the wave form B represents the pattern of electric signals 17 and 18 generated by a photodiode 19 (FIGS. 1 and 2) to represent predetermined fractions 20 and 21 of the monochromatic excitation light signals 8 and 9.

Both the succession of electrical emitted light signals 14 and 16 and the succession of electrical reference signals 17 and 18 are transferred by the photomultiplier 13 and photodiode 19 respectively to the electronic processor 5 where two memory amplifiers 22 and 23, also known as "buffer memories", amplify and memorise them. The successions of signals are then compared in a signal normaliser 24 which, comparing the emitted light signals 14 and 16 with the signals representing excitation light 17 and 18, produces output signals 25 and 26 which correspond completely to the signals 14 and 16 but also take into account, and are compensated for, any small variations in the intensity of excitation light emitted by the monochromator 1.

The normalised signals 25 and 26 are then integrated in an integrator divider 27 which takes the mean of all signals 25 and all signals 26 so as to provide respective mean signals 28 and 29 which are free from small variations due to slight variations in operation of the parts of the apparatus which have generated them, such as in particular the photomultiplier 13, which notably usually operates by counting photons.

Finally the mean signals 28 and 29, which may also be visualised separately in respective output visualisers 30 and 31, are compared and the second signal is subtracted from the first in a differentiator 32, which provides a signal output signal 33 presented visually by an output visualiser (of analogue or digital type) 34.

Since the signal 28 represents the useful monochromatic emission signal of the molecule under examination with a superimposed spurious signal determined by the diffused light and by any spurious monochromatic light emitted by traces of other molecules contained in the sample substance, and the signal 29 only represents the spurious signal (with the same value), it is evident that the result of the subtraction carried out in the differentiator 32 is the desired useful signal, completely freed of superimposed spurious signals. The useful signal is shown in the wave form D in FIG. 5.

What is claimed is:

1. A process for measuring the concentration of a molecule of selective spectrum in a sample substance, comprising subjecting the sample substance to a first monochromatic excitation light of wavelength lying within the absorption spectrum of the molecule under measurement, filtering and collecting a first light emission from the sample substance at a wavelength lying within the emission spectrum of the molecule, and determining the intensity of the monochromatic light collected, and further comprising subsequently subjecting the sample substance to a second monochromatic excitation light of a wavelength close to that of the first monochromatic light but outside the absorption and emission spectra of the molecule, filtering and collecting a corresponding second light emission from the sample substance at the same wavelength as the first, then determining the new intensity of collected light and subtracting this from the first to give a useful monochromatic light signal free from spurious signals due to diffused light or to spurious fluorescent or phosphorescent light due to traces of other molecules in the sample substance.

2. A process as claimed in claim 1, wherein said secondmonochromatic excitation light has a wavelength lying between the absorption and emission spectra of the molecule.

3. A process as claimed in claim 1, wherein said second monochromatic excitation light has a wavelength greater than those within the emission spectrum of the molecule.

4. A process as claimed in claim 1, comprising a time interval of approximately 0.1–10 $\mu$sec between the first and second monochromatic excitation light.

5. An apparatus for measuring the concentration of a molecule of selective spectrum in a sample substance, comprising an excitation monochromator arranged to subject the sample substance to a first and subsequently to a second monochromatic excitation light of wavelengths which are close together but which are within the absorption spectrum of the molecule being measured and outside the absorption and emission spectra of the same molecule respectively, a collection monochromator arranged to filter and collect corresponding light emissions from the sample substance at a wavelength within the molecule emission spectrum, and electronic processing means arranged to determine the collected light intensities corresponding to said emissions and subtract one from the other.

6. An apparatus as claimed in claim 5, wherein said collection monochromator comprises a narrow band inlet filter and a photomultiplier arranged to amplify and convert the light intensities emitted by the sample substance and filtered through said inlet filter into corresponding electrical emitted light signals.

7. An apparatus fo measuring the concentration of a molecule of selective spectrum in a sample substance, comprising an excitation monochromator arranged to subject the sample substance to a first and subsequently to a second monochromatic excitation light at wavelengths which are close together but which are within the absorption spectrum of the molecule being measured and outside the absorption and emission spectra of the same molecule respectively, a collection monochromator arranged for filtering and collecting corresponding light emissions from the sample substance at a wavelength within the molecule emission spectrum, and electronic processing means arranged for determining collected light intensities corresponding to said emissions and subtracting one from the other, wherein said electronic processing means comprise memory means for memorizing electrical signals representing the excitation light intensities of said corresponding light emissions, signal normalising means arranged to compare said electrical signals for generating normalised signals insensitive to variations in excitation light intensity, integrator divider means arranged for taking the mean of said normalised signals produced from the first monochromatic excitation light and of the normalised signals produced subsequently by the second monochromatic excitation light, and differentiator means arranged to subtract the mean signal produced by the second monochromatic excitation light from the mean signal produced by the first monochromatic excitation light for generating a single signal constituting the useful monochromatic light signal emitted by the molecule under examination.

8. An apparatus as claimed in claim 7, wherein said collection monochromator comprises a narrow band inlet filter and a photomultiplier arranged to amplify and convert the light intensities emitted by the sample substance and filtered through said inlet filter into said corresponding electrical emitted light signals.

* * * * *